(12) United States Patent
Erickson et al.

(10) Patent No.: US 10,241,233 B2
(45) Date of Patent: Mar. 26, 2019

(54) METHODS AND APPARATUS FOR MONITORING INTERACTIONS BETWEEN PARTICLES AND MOLECULES USING NANOPHOTONIC TRAPPING

(71) Applicant: CORNELL UNIVERSITY, Ithaca, NY (US)

(72) Inventors: David Erickson, Ithaca, NY (US); Pilgyu Kang, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/824,423

(22) Filed: Aug. 12, 2015

(65) Prior Publication Data

US 2016/0047944 A1 Feb. 18, 2016

Related U.S. Application Data

(60) Provisional application No. 62/036,219, filed on Aug. 12, 2014.

(51) Int. Cl.
| | | |
|---|---|---|
| *G01N 21/47* | (2006.01) | |
| *G01N 21/25* | (2006.01) | |
| *G02B 1/00* | (2006.01) | |
| *G02B 21/32* | (2006.01) | |
| *G01N 33/542* | (2006.01) | |
| *G21K 1/00* | (2006.01) | |

(52) U.S. Cl.
CPC ............ *G02B 1/005* (2013.01); *G01N 21/25* (2013.01); *G01N 21/47* (2013.01); *G01N 33/542* (2013.01); *G02B 21/32* (2013.01); *G21K 1/006* (2013.01)

(58) Field of Classification Search
None
See application file for complete search history.

(56) References Cited

U.S. PATENT DOCUMENTS

2015/0111199 A1* 4/2015 Hart .................. G01N 21/47
435/5

OTHER PUBLICATIONS

Yin-Fan Chen et al., Controlled Photonic Manipulation of Proteins and Other Nanomaterials, Nano Letters 2012, vol. 12, pp. 1633-1637, pubs.acs.org/NanoLett, ACS Publications, 2012 American Chemical Society.
(Continued)

*Primary Examiner* — Neil N Turk
(74) *Attorney, Agent, or Firm* — Bond, Schoeneck & King, PLLC; Erin Phillips; William Greener

(57) ABSTRACT

A method for characterizing an interaction between a first particle and a second particle is provided. The method includes the steps of: (i) providing an optical trap system including a photonics-based trap, a light source, and a camera; (ii) optically trapping, using the photonics-based trap, the first particle; (iii) obtaining a first measurement of a trap stiffness of the photonics-based trap; (iv) introducing the second particle to the optically trapped particle; (v) incubating the first and second particles under conditions suitable for an interaction between the first and second particles; (vi) obtaining a second measurement of the trap stiffness of the photonics-based trap after the incubation; and (vii) determining, using the first measurement of trap stiffness and the second measurement of trap stiffness, a property of the interaction between the first particle and the second particle.

1 Claim, 7 Drawing Sheets

(56) References Cited

OTHER PUBLICATIONS

Erickson et al., Nanomanipulation using near field photonics, Lab on a Chip—Micro- & nano-fluidic research for chemistry, physics, biology, & bioengineering, vol. 11, No. 6, Mar. 21, 2011, pp. 995-1009, RSC Publishing.

* cited by examiner

METHODS AND APPARATUS FOR MONITORING INTERACTIONS BETWEEN PARTICLES AND MOLECULES USING NANOPHOTONIC TRAPPING

CROSS-REFERENCE TO RELATED APPLICATIONS

This application claims priority to U.S. Provisional Patent Application Ser. No. 62/036,219, filed on Aug. 12, 2014 and entitled "Nanophotonic Interaction Measurements of Freely Binding Biomolecules," the entire disclosure of which is incorporated herein by reference.

GOVERNMENT FUNDING

This invention was made with Government support under Grant Number 1R01GM106420-01 awarded by the NIH; Grant Number ECCS-0335765 awarded by the NSF; and Grant Number DMR-1120296 awarded by the NSF MRSEC program. The United States Government has certain rights in the invention.

FIELD OF THE INVENTION

The present disclosure is directed generally to methods and systems for label-free analysis of molecular interactions using near-field optical techniques.

BACKGROUND

Analyzing and understanding molecular interactions is fundamentally important to the life sciences. Exploring these interactions will not only advance the understanding of basic biology, but will provide researchers with the ability design molecules to modify, block, or otherwise affect certain interactions.

There are currently numerous methods available to analyze molecular interactions, including both labeled and label-free mechanisms. Labeling methods include fluorescence, radioactivity, phosphorescence, bioluminescence, and chemiluminescence, among others. Label-free methods include surface plasmon resonance, differential scanning calorimetry, various biosensors such as capacitive, conductometric, and impedimetric sensors, among many other methods. However, these common approaches typically require immobilizing one or both of the interacting molecules on a sensing area such as an assay plate or a sensor surface, thereby constraining their binding activity. When analyzing multivalent bindings, for example, this restriction prevents an accurate measurement of affinity and binding capacity.

Accordingly, there is a continued need in the art for methods and systems that allow for label-free analysis of free-solution molecular interactions with increased resolution.

SUMMARY OF THE INVENTION

The present disclosure is directed to inventive methods and systems for detecting unrestricted interactions between molecules. A near-field optical trap is utilized to provide quantitative analysis of the interactions at, for example, the attogram scale. The method exploits the fact that the optical force exerted on a trapped particle is proportional to the particle's volume and polarizability. The spring constant or the trap stiffness can be extracted from the Brownian fluctuation of the trapped particle. Thus, by observing these fluctuations, the binding of a partner biomolecule to the trapped particle can be detected. For example, specific antibody binding to an optically trapped virus is detected by analyzing changes in the confined Brownian motion of the virus observed via evanescent wave light scattering. The method allows the measurement of binding interactions without restricting them by immobilizing or labeling either of the interacting biomolecules. In addition, the developed model for the effective polarizability of the binding complex enables accurate measurements of the affinity and stoichiometry of the interactions.

According to one embodiment, the label-free method for analyzing molecular interactions can be used to analyze the potential pathogenicity and virulence of rapidly mutating influenza viruses, in addition to identification. Furthermore, the light-scattering-based detection method can be used to monitor biomolecular interactions in real time, giving new information on the kinetics of the interaction at a single molecule level. The methods and systems described herein have many potential applications, including in drug discovery for screening, developing drug compounds, and in clinical diagnosis as a label-free ultrasensitive biosensor, among many other applications.

Generally, in one aspect, a method for characterizing an interaction between a first particle and one or more second particles is provided. The method includes the steps of: (i) providing an optical trap system including a photonics-based trap, a light source, and a camera; (ii) optically trapping, using the photonics-based trap, the first particle; (iii) obtaining a first measurement of a trap stiffness of the photonics-based trap; (iv) introducing the one or more second particles to the optically trapped particle; (v) incubating the first and second particles under conditions suitable for an interaction between the first and second particles; (vi) obtaining a second measurement of the trap stiffness of the photonics-based trap after the incubation; and (vii) determining, using the first measurement of trap stiffness and the second measurement of trap stiffness, a property of the interaction between the first particle and the second particle.

According to an embodiment, the photonics-based trap is, for example, a photonic crystal resonator, a photonic waveguide, a plasmonic structure, or an optically-excited nanostructure or micro-structure.

According to an embodiment, the step of obtaining a first measurement of a stiffness of the photonics-based trap comprises the step of analyzing reduced Brownian motion of the first particle in the photonics-based trap.

According to an embodiment, the trap stiffness of the photonics-based trap is extracted from a positional variance of the particle within the photonics-based trap.

According to an embodiment, the positional variance of the particle within the photonics-based trap is determined at least in part using image analysis. According to an embodiment, the image analysis is video tracking.

According to an embodiment, the first particle is between 10 nm and 20 μm.

According to an embodiment, the method includes the step of determining an affinity between the first particle and the second particle.

According to an embodiment, the method includes the step of determining a stoichiometric relationship between the first particle and the second particle.

According to an embodiment, the system obtains multiple measurements of the trap stiffness during the incubation, and determines the rate of the interaction between the first particle and the second particle.

According to an aspect, a method for characterizing an interaction between a first particle and one or more second particles is provided. The method includes the steps of: (i) optically trapping the first particle; (ii) obtaining a first measurement of a trap stiffness of the trap; (iii) introducing the one or more second particles to the optically trapped particle; (iv) incubating the first and second particles under conditions suitable for an interaction between the first and second particles; (v) obtaining a positional variance of the trapped molecule after incubation with the second particle; and (vi) determining, using the positional variance, a property of the interaction between the first particle and the second particle.

According to an embodiment, the positional variance is obtained using a near-field light scattering imaging system.

According to an aspect is a system configured to characterize an interaction between a first particle and one or more second particles. The system includes: (i) a first particle; (ii) a second particle; (iii) a photonics-based optical trap; (iv) a camera configured to detect a positional variance of an optically trapped particle in the photonics-based trap; and (v) a processor configured to receive a first measurement of a trap stiffness of the photonics-based trap, receive a second measurement of the trap stiffness of the photonics-based trap after the second particle is incubated with the first particle, and determine, using the first measurement of trap stiffness and the second measurement of trap stiffness, a property of the interaction between the first particle and the second particle.

These and other aspects of the invention will become clear in the detailed description set forth below.

BRIEF DESCRIPTION OF THE DRAWINGS

In the drawings, like reference characters generally refer to the same parts throughout the different views. Also, the drawings are not necessarily to scale.

DETAILED DESCRIPTION OF EMBODIMENTS

The present disclosure is directed to embodiments of a method and system for detecting unrestricted interactions between molecules using a near-field optical trap. Since the optical force exerted on a trapped particle is proportional to the particle's volume and polarizability, and the spring constant or the trap stiffness can be extracted from the Brownian fluctuation of the trapped particle, the binding of a partner molecule to the trapped particle can be detected.

For example, according to an embodiment, the near-field optical trap method and system can be utilized to analyze many different specific biomolecular interactions, including but not limited to antibody/virus interactions. As described in detail below, the near-field optical trap method and system can detect interactions between single influenza viruses and antibodies at the attogram scale. Specific antibody binding to an optically trapped virus is detected, for example, by analyzing changes in the confined Brownian motion of the virus observed via evanescent wave light scattering. This same technique can be applied to a wide range of molecular interactions because the nanophotonic tweezer can handle molecules from tens to thousands of nanometers in diameter.

Figure 1:
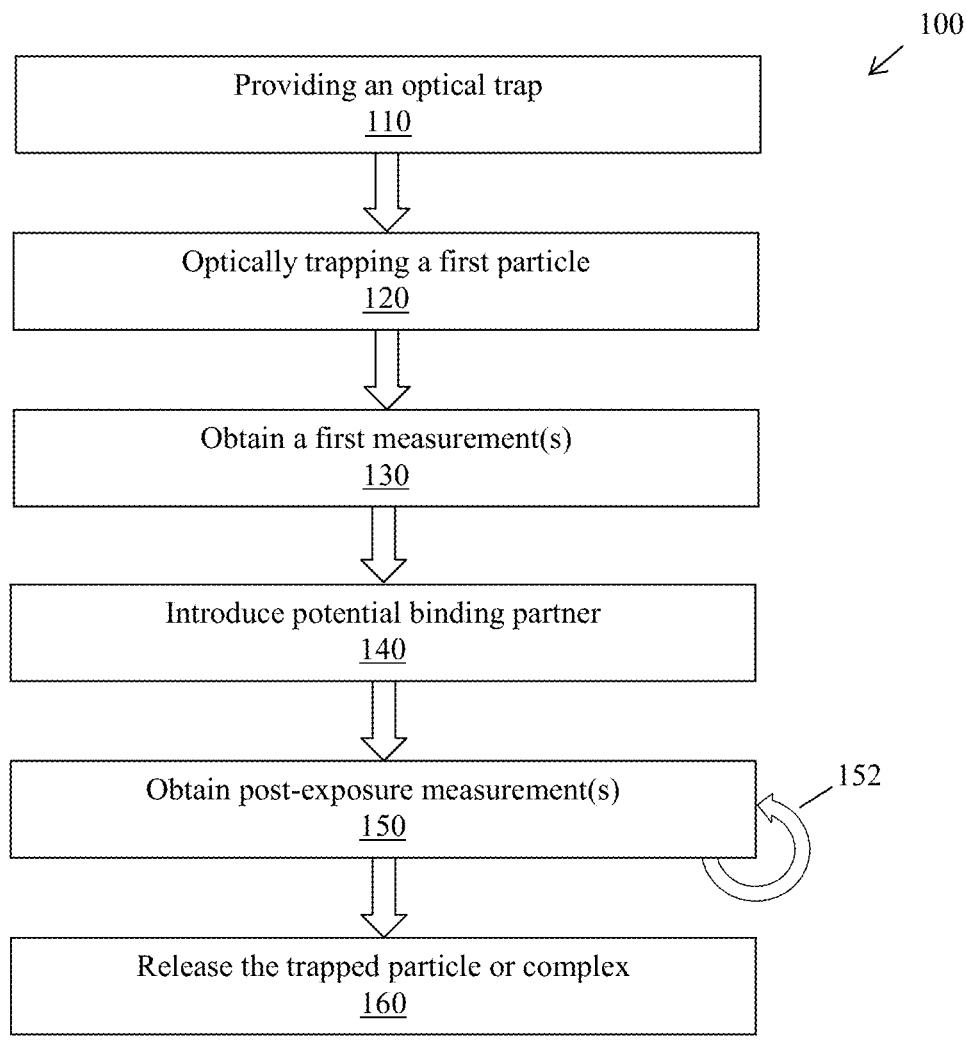
FIG. 1 is a flowchart of a method for label-free method for analyzing molecular interactions, in accordance with an embodiment.

Referring to FIG. 1, in one embodiment, is a method 100 for analyzing and quantifying interactions between two or more particles. The particles analyzed by this method can be, for example, a biological particle such as a virus, cell, protein, protein aggregate, and many other types of biological particles, or can be a non-biological particle such as a polymeric, glass, or metallic nanoparticle. Many other types of biological and non-biological particles are possible. The interactions analyzed and/or quantified by the methods described or otherwise envisioned herein can be any type of interaction between the two or more particles. For example, the interaction can be binding such as specific or non-specific binding, rate of binding, rate of absorption, unbinding, and desorption, among many others. The interaction analyzed and/or quantified can also be, for example, the lack of an interaction.

Figure 2A:
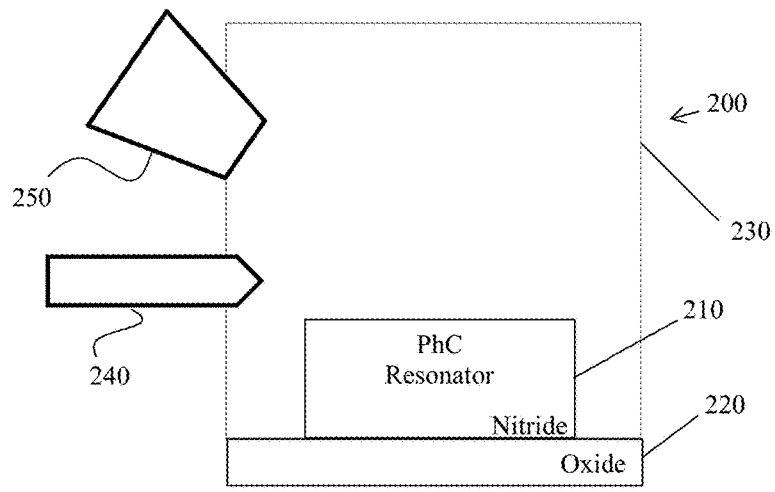
FIG. 2A is a schematic representation of a photonic crystal resonator system, in accordance with an embodiment.
Figure 2B:
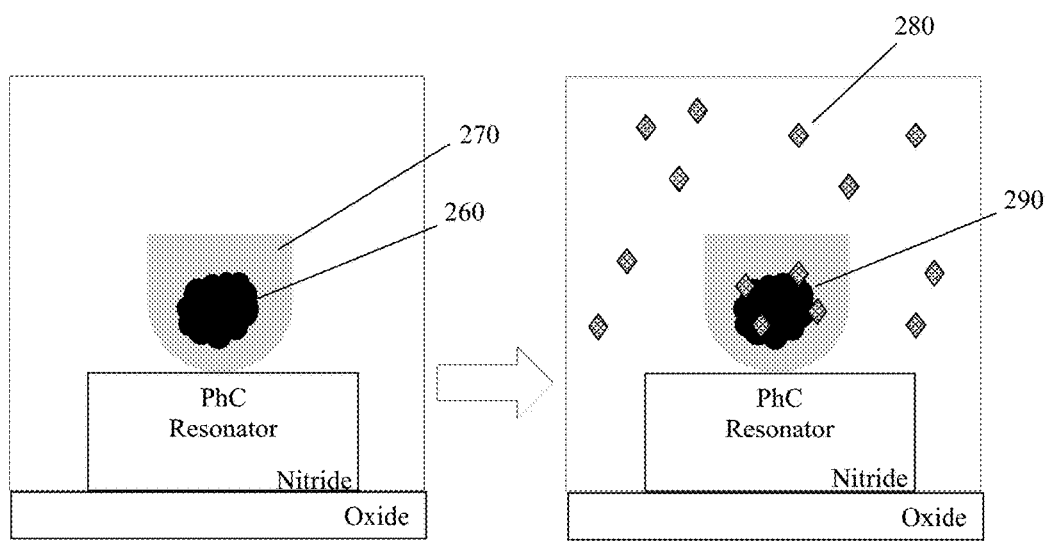
FIG. 2B is a schematic representation of a photonic crystal resonator system with an optically trapped particle, in accordance with an embodiment.
Figure 3:
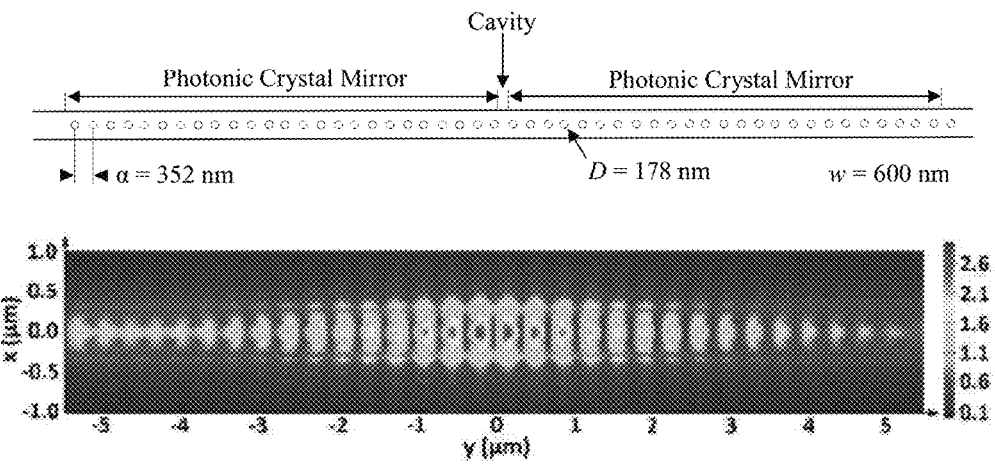
FIG. 3 is a schematic representation of a scanning electronic microscopy image of a photonic crystal resonator (top) and a schematic representation of the strong field confinement within the resonator cavity (bottom), in accordance with an embodiment.

At step 110 of the method, an optical trap is provided. The optical trap can be any of the devices described herein or otherwise envisioned. For example, the optical trap is a photonic crystal ("PhC") resonator, as shown in FIGS. 2-3, and/or a photonic waveguide, a plasmonic structure, or any other optically excited nano or micro-structure. According to one embodiment, the silicon nitride PhC resonator comprises a series of holes on both sides of a resonator cavity and a central hole. The holes may be etched in a silicon nitride waveguide lying on a silicon dioxide substrate, although other materials are possible. As shown in FIG. 3, for example, according to an embodiment, the holes are spaced at approximately 352 nm, although the distance is variable. For example, the periodicity of the PhC structure is kept constant, and the hole sizes can be chosen to have a Gaussian-shaped field attenuation inside the Bragg mirror and have a desired resonant wavelength. According to an embodiment the PhC resonator comprises a small hole at the center of the cavity such that the superposition of evanescent fields leads to an increase in the field intensity and thus the trapping stiffness is significantly increased. Many other variations of the optical trap are possible. For example, according to one embodiment, the PhC is a component of a microarray utilized to simultaneously or sequentially analyze multiple interactions. Referring to FIG. 2A, in one embodiment, is a PhC resonator system 200 including a PhC resonator 210, an oxide base 220 such as a silicon dioxide substrate, and a chamber 230. According to an embodiment, chamber 230 allows solutions and/or molecules to be introduced for trapping, binding, washing, and other purposes. The PhC resonator system 200 may also include a light source 240, such as a laser, configured to emit light to trap a molecule on the PhC resonator 210. The system can also include a camera 250 or other visualization device for obtaining images or other data of the system for analysis.

At step 120 of the method, a particle is optically trapped. For example, the particle may be introduced into chamber 230 or otherwise introduced to the system. According to one embodiment, the PhC resonator 210 is situated within a chamber comprising multiple copies of the target particle, or just a limited number of copies of the target particle. The light source 240 can be utilized to excite the resonator, causing the particle to be propelled by the optical force to the center of the cavity while it is trapped on the resonator surface. Referring to FIG. 2B, for example, particle 260 is trapped on PhC resonator 210 by light source 240 emitting light 270.

At step 130 of the method, one or more initial measurements are obtained. For example, according to an embodiment, an initial measurement of the trap stiffness is conducted. Referring to FIG. 2B, for example, where particle 260 is optically trapped, trap stiffness can be measured. According to an embodiment, in order to determine the stiffness of the optical trap, the reduced Brownian motion of the particle trapped at the center of the cavity is analyzed, including as described in greater detail below.

According to another embodiment, the first particle is not optically trapped using the PhC resonator, but the position of the particle is observed using a near-field light scattering technique. Using this method, neither of the interacting biomolecules is immobilized.

At step 140 of the method, a second particle is introduced. The second particle can be any particle, including but not limited a binding partner such as a known binding partner, a suspected binding partner, or a possible binding partner, such as in the case of a screen for molecular interactions. The second particle can be one particle, or can be many particles. For example, according to an embodiment, two or more different types of particles are introduced at step 140 of the method. The second particle(s) can be introduced, for example, by introducing a flow to the chamber where the PhC resonator resides. Referring to the right panel in FIG. 2B, for example, where particle 260 is optically trapped, second particle 280 is introduced to chamber 230. If the conditions are suitable for a biomolecular interaction, the first particle 260 and one or more of the second particles 280 will bind. This will increase, for example, the radius of the complex 290, shown in FIG. 2B.

According to just one embodiment, for example, the flow in a microchannel is switched from virus solution to antibody dispersed solution at step 140. Antibodies in the following solution bind to the trapped virus. The binding can be saturated for a period of time, such as 30 min, after the flow switching.

At step 150 of the method, one or more post-exposure measurements are obtained. For example, according to an embodiment, an measurement of the trap stiffness is conducted. Referring to the right panel in FIG. 2B, for example, where particle 260 is optically trapped, trap stiffness can be measured for the complex 290. According to an embodiment, in order to determine the stiffness of the optical trap, the reduced Brownian motion of the complex 290 trapped at the center of the cavity is analyzed, including as described in greater detail below.

According to an embodiment, the relationship between the change in the particle radius between particle 260 and complex 290, and the trap stiffness, is analyzed. The relative trap stiffness of the complex after binding is related to that of the particle before binding, as described in greater detail below. Accordingly, if the refractive indices of the trapped particle and binding antibody are known, specific binding characterized by the change in radius corresponding to the bound layer is detected by measuring the relative trap stiffness. According to an embodiment, the stoichiometry of the binding can also be determined from the obtained measurements.

According to an embodiment, as shown by arrow 152 in FIG. 1, step 150 can be repeated two or more times. For example, the system can be utilized to analyze kinetics of the interaction between the two or more particles. Rather than making an initial measurement of the trap stiffness before binding and then a final measurement after binding, the system can be configured to take multiple measurements at step 150. For example, the system can be configured to take measurements in a time-dependent manner. In one embodiment, the system can be configured to take time-dependent measurements depending on the expected or suspected kinetics of the possible interaction(s). Rate of binding or any other interaction can then be extracted from the multiple obtained measurements using known techniques.

At step 160 of the method, the trapped particle 260, or complex 290 if a complex formed, is released from the optical trap. This occurs when the light source is deactivated or otherwise adjusted.

According to an embodiment, the system comprises a processor which is configured to receive a first measurement of a trap stiffness of the optical trap, receive a second measurement of the trap stiffness of the optical trap after the second particle is incubated with the first particle, and determine, using the first measurement of trap stiffness and the second measurement of trap stiffness, a property of the interaction between the first particle and the second particle.

According to an embodiment, the methods and systems described and otherwise envisioned herein are used for multiplexed analysis of multiple interactions. For example, the optical trapping system can comprises multiple optical devices, or multiple optical traps, in an array. The array can then monitor multiple interactions at the same time. According to one embodiment, an array comprises multiple optical traps that each trap a first particle. Each of the traps is isolated within the array such that a different second particle can be introduced individually to different chambers. In this way, interactions between a first particle and multiple different second particles are analyzed. According to another embodiment, an array comprises multiple optical traps that each trap different first particles. A second particle is then added to the array. In this way, interactions between multiple different first particles and a second particle are analyzed. Many other configurations are possible.

Accordingly, methods and systems are described herein to directly and accurately detect the binding of unrestricted molecules using near-field optical trapping. The methods and systems also demonstrate the ability to measure the affinity and stoichiometry of molecular interactions at the attogram scale. According to an embodiment, and where comparison is possible, measurements of the affinity and the stoichiometry of a specific antibody to the colloid are in agreement with the manufacturer-quoted binding capacity. Notably, the detection method does not require labeling or immobilizing either of the interacting molecules. As described in detail below, affinity measurements for a single influenza virus and an anti-influenza antibody are obtained, which is found to be 6.8 (±1.1) attogram of anti-influenza antibodies per virus.

According to an embodiment, the method can be utilized for studying the potential pathogenicity and virulence of rapidly mutating influenza viruses in addition to identification. Furthermore, the light-scattering-based detection method can be used to monitor biomolecular interactions in real time, giving new information on the kinetics of the interaction at a single molecule level. Because a very high optical intensity is available at the center cavity of the photonic crystal resonator, the methods are able to observe scattered light signals from sub-100 nm particles. This technique has many potential applications, including but not limited to drug discovery for screening and developing drug compounds, clinical diagnosis as a label-free ultrasensitive biosensor, and many other applications.

Example 1

According to an embodiment, the near-field optical trap method and system can be utilized to investigate interactions between, for example, a pathogenic virus and its antibody. Understanding these interactions is vital to pathogen control and prevention. By observing Brownian fluctuations of a trapped particle, the spring constant or the trap stiffness can be extracted, and the binding of a partner biomolecule to the trapped particle can be detected. This allows for analysis of binding interactions without restricting them by immobilizing or labeling either of the interacting biomolecules. In addition, the inventive model for the effective polarizability of the binding complex enables accurate measurements of the affinity and stoichiometry of the interactions.

According to an embodiment, therefore, is an antibody binding assay in which one interacting antibody is coupled to the surface of a nanoparticle and the partner antibody freely moving in a solution is allowed to bind to it. The affinities and stoichiometries measured affinities and stoichiometries using the near-field optical trap method and system can then be compared to known values. Further, binding interactions can be analyzed using a system in which neither of the interacting biomolecules is immobilized. For example, the system can detect the binding of antibody to a single human influenza A virus, and can measure the stoichiometry of the specific antibody.

According to an embodiment, the result of the molecular binding to the target is described using an effective sphere model of antibody-particle complexes. The effective polarizability of the sphere allows one to describe the interactions with the known applied optical force from the following equation:

$$F_{trap} = 2\pi \nabla I_o \alpha_{eff}/c \quad \text{(Eq. 1)}$$

where $c$ and $\lambda$ are the speed and wavelength of light, $I_o$ is the incident intensity, and $\alpha_{eff}$ is the effective polarizability expressed according to the following equations:

$$\alpha_{eff} = 4\pi\varepsilon_0 \left(\frac{\varepsilon_e - \varepsilon_m}{\varepsilon_e + 2\varepsilon_m}\right) R_{outer}^3 \text{ where} \quad \text{(Eq. 2)}$$

$$\varepsilon_e = \varepsilon_s \left(\frac{R_{outer}^3(\varepsilon_e + 2\varepsilon_s) + 2R_{inner}^3(\varepsilon_c - \varepsilon_s)}{R_{outer}^3(\varepsilon_c + 2\varepsilon_s) - R_{inner}^3(\varepsilon_c - \varepsilon_s)}\right) \quad \text{(Eq. 3)}$$

where $\varepsilon_c$, $\varepsilon_s$, and $\varepsilon_m$ are dielectric constants of the core (polystyrene or a virus), shell (antibodies), and medium (water) respectively, $\varepsilon_e$ is the effective dielectric constant of the core-shell complex ($\varepsilon \approx n^2$ assuming non-absorbing materials of refractive indices such as 1.59 for a polystyrene (PS) particle, 1.41 for an antibody, and 1.48 for an influenza virus), $R_{outer}$ is the core-shell radius, and $R_{inner}$ is the core radius. The force is calibrated with its spring constant or the trap stiffness.

At a step of the method as described above, a particle is optically trapped. Referring to FIG. 3, according to an embodiment, is a schematic representation of a scanning electron microscope image of a photonic crystal ("PhC") resonator. A particle is optically trapped using the PhC resonator and the equipartition method is utilized to extract the trap stiffness from the positional variance of the particle within the optical trap using video tracking analysis. According to an embodiment, the silicon nitride PhC resonator was fabricated according to the procedure set forth in Chen et al., *Controlled Photonic Manipulation of Proteins and Other Nanomaterials*, Nano Lett 12:1633-1647 (2012) (the entire contents of which are hereby incorporated by reference), with several important modifications. NEB-31 electron beam photoresist was spun on a wafer on which a 250-nm stoichiometric silicon nitride layer was deposited on top of a 3.5 gm thermal oxide layer by the low-pressure chemical vapor deposition. To reduce a charging effect during exposure, a 5-10 nm thin gold film was deposited on the resist with a thermal evaporator. It was patterned using a JEOL 9500 electron beam lithography system.

According to an embodiment, a 1064 nm fiber coupled diode laser (LU1064M400, Lumics, El Segundo, Calif.) was used as a light source for optical trapping. The laser was coupled to the input waveguide of silicon nitride through a lensed optical fiber. A thermistor in the laser diode was controlled to tune in a resonance wavelength of a photonic crystal resonator with an increase of approximately 0.3 nm per 1 K temperature rise. The power coupled into the resonator was measured by focusing the light emitting from output waveguide onto a detector of a power meter. Power measurements with a power meter were sampled in real time using a Labview program. A polarizer passing a TE-polarized light was placed between the focusing lens and the detector.

At a step of the method as described above, the relationship between the change in the particle radius and the trap stiffness is analyzed. The relative trap stiffness of the complex after binding is related to that of the particle before binding with the relative polarizabilities expressed as:

$$(k_{trap,\Delta R}/P_{\Delta R})/(k_{trap,0}/P_0) = \alpha_{eff,\Delta R}/\alpha_{eff,0} \quad \text{(Eq. 4)}$$

where $P$ is the power, $k_{trap}$ is the trap stiffness, subscript 0 denotes an initial measurement, and subscript $\Delta R$ denotes the measurement at equilibrium. Therefore, if the refractive indices of the trapped particle and binding antibody are known, specific binding characterized by the change in radius corresponding to the bound layer, $\Delta R$, is detected by measuring the relative trap stiffness. This relationship is described by the transcendental equation:

$$R_{outer,\Delta R} = R_{outer} + \Delta R = \left[ \frac{\left(\frac{k_{trap,\Delta R}}{P_{\Delta R}}\right)}{\left(\frac{k_{trap,0}}{P_0}\right)} \cdot \left(\frac{\varepsilon_{e,0} - \varepsilon_m}{\varepsilon_{e,0} + 2\varepsilon_m}\right) \right]^{1/3} \cdot R_{outer} \quad \text{(Eq. 5)}$$

where $k_{trap} = 2k_B T / r_{rms}^2$, where $k_B$ is the Boltzmann constant, T is the temperature in K, and $r_{rms}^2 = (1/n)\Sigma(x^2+y^2)$ is the variance of n instantaneous positions, and all other variables are noted as previously.

Figure 4:
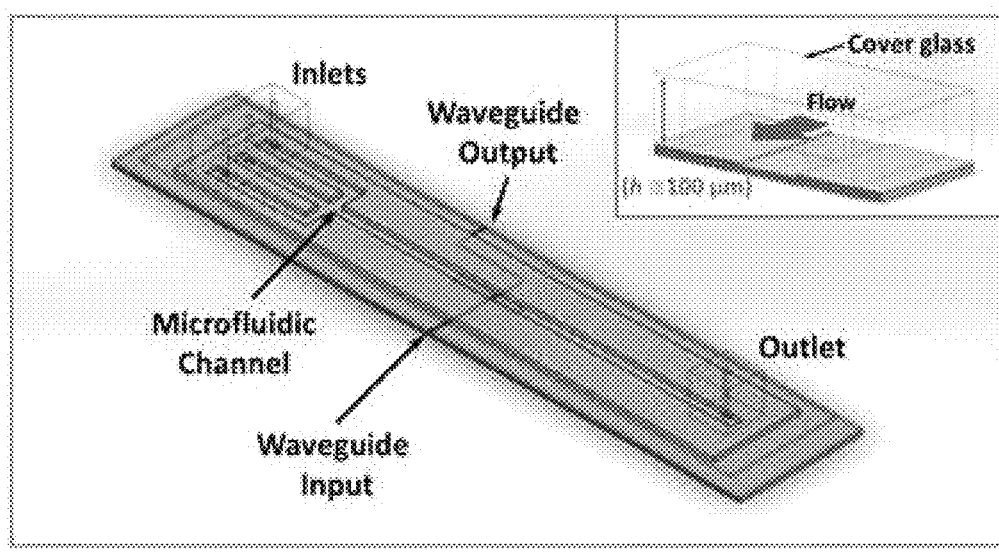
FIG. 4 is a schematic representation of an integrated optofluidic device, in accordance with an embodiment.

According to an embodiment, the power-normalized relative trap stiffness for equilibrium binding affinity is determined after an incubation period of approximately 30-min. During this time, the solution of binding antibody is flowed over a trapped particle using a microfluidic channel. Referring to FIG. 4, in one embodiment, is an integrated optofluidic device. According to an embodiment, to make flow channels, three holes of D=500 nm were cut on a glass coverslip using a $CO_2$ laser (VersaLaser VLS3.50). Punched PDMS piece was bonded to the punched cover glass by oxygen plasma bonding. A 100-μm thick parafilm spacer was cut using the CO2 laser to have three inlet channels combining to one channel whose width is approximately 1 mm. The parafilm spacer was laid between the cover glass and a fabricated nitride chip. Next the sandwiched complex was briefly heated on a 100-degree-Celsius hot plate to melt the parafilm spacer and bond firmly for preventing leaking in flowing and switching solutions. Tygon tubings were inserted tightly to the holes through PDMS fixtures to inject solutions into the channels using three syringe pumps (Harvard Apparatus, Holliston, Mass.). Before conducting an experiment, a SuperBlock blocking buffer solution (Sigma-Aldrich, 37580) with 0.05% tween 20 (Sigma-Aldrich, P7949) was filled in the channels and incubated either over 30 min at room temperature or over 12 hours at 2-8 degree Celsius to prevent non-specific binding.

Figure 5:
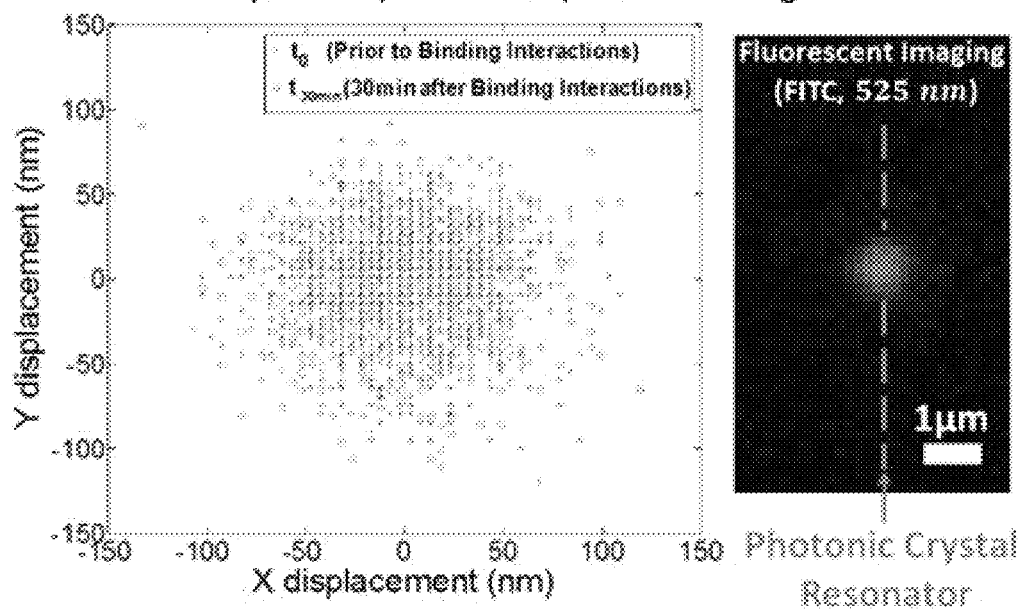
FIG. 5 is a graph tracking trajectories within an optical trap before and after binding of mouse IgM to goat anti-mouse IgG coated on the surface of fluorescent polystyrene particle (left panel), and an image captured by a CCD camera showing a IgG-coated colloid trapped at the resonator cavity (right panel), in accordance with an embodiment.
Figure 6:
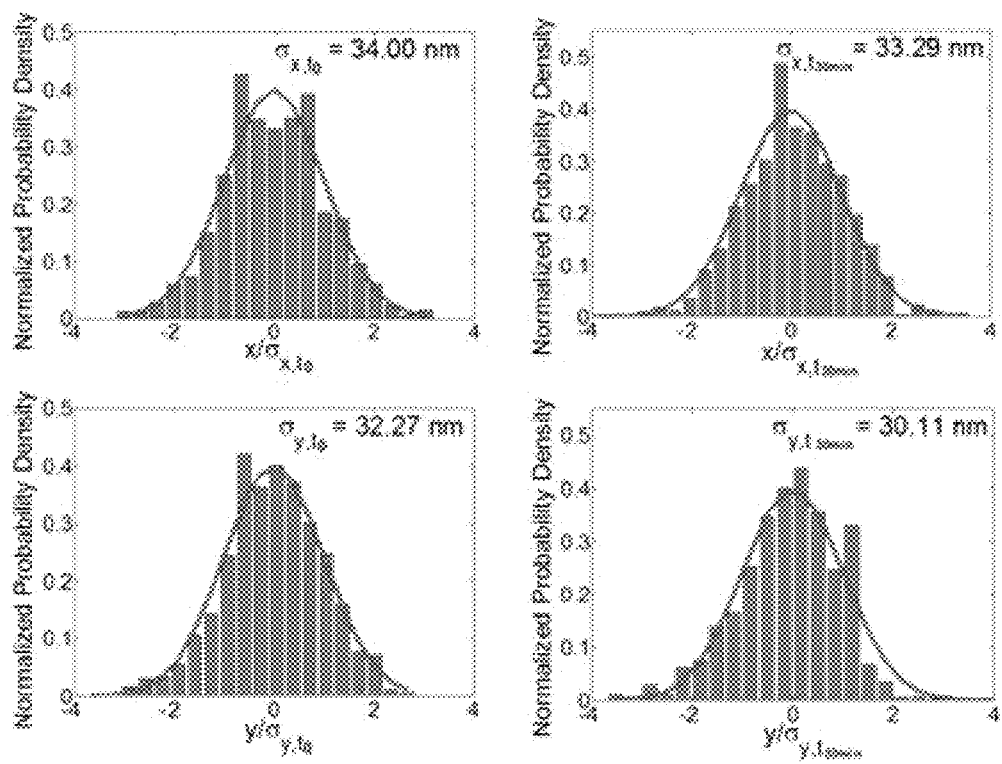
FIG. 6 is a graph of probability density histograms of x (top) and y (bottom) displacements before (left) and after (right) bindings with mouse IgM, where curves are Gaussian fits to the histograms, in accordance with an embodiment.

According to an embodiment, a specific binding between a fluorescent polystyrene bead coated with goat anti mouse IgG and antibodies in solution was measured. The measured binding capacity of the antibodies was compared to the manufacturer's quoted value (Spherotech Inc.). The position fluctuations were measured using fluorescence microscopy, an example of which is shown in FIG. 5, with typical measurements using this setup shown in FIG. 6.

Changes in power-normalized trap stiffness and radius increases of an IgG coated colloid were compared for solutions of mouse IgG, mouse IgM, goat anti-rabbit IgG, and a buffer. As described above, the power-normalized relative trap stiffness was correlated to the radius increase with a known initial diameter for $R_{outer}$ (D≈270 nm). From studies on protein sizes, changes in thickness resulting from specific antibody binding were predicted to be 5.79 nm for IgG ($M_{IgG}$=160.5 kDa) and 10.55 nm for IgM ($M_{IgM}$=970 kDa). Affinity is indicated by a measured radius increase 7.5±6.5 nm and 14.4±5.6 nm for solutions of mouse IgG and mouse IgM respectively, in agreement with the predictions. It should be noted that theoretical estimates are based on the unhydrated mass of protein while in the experiment there are water molecules bound to the antibody. Electrical measurements indicate an increase of about 4.5 nm for IgG. Specificity is demonstrated by measured negligible radius increases of −1.7±6.6 nm and −2.2±5.7 nm in the solution of an unspecific antibody (goat anti-rabbit IgG) and a buffer respectively.

Figure 7:
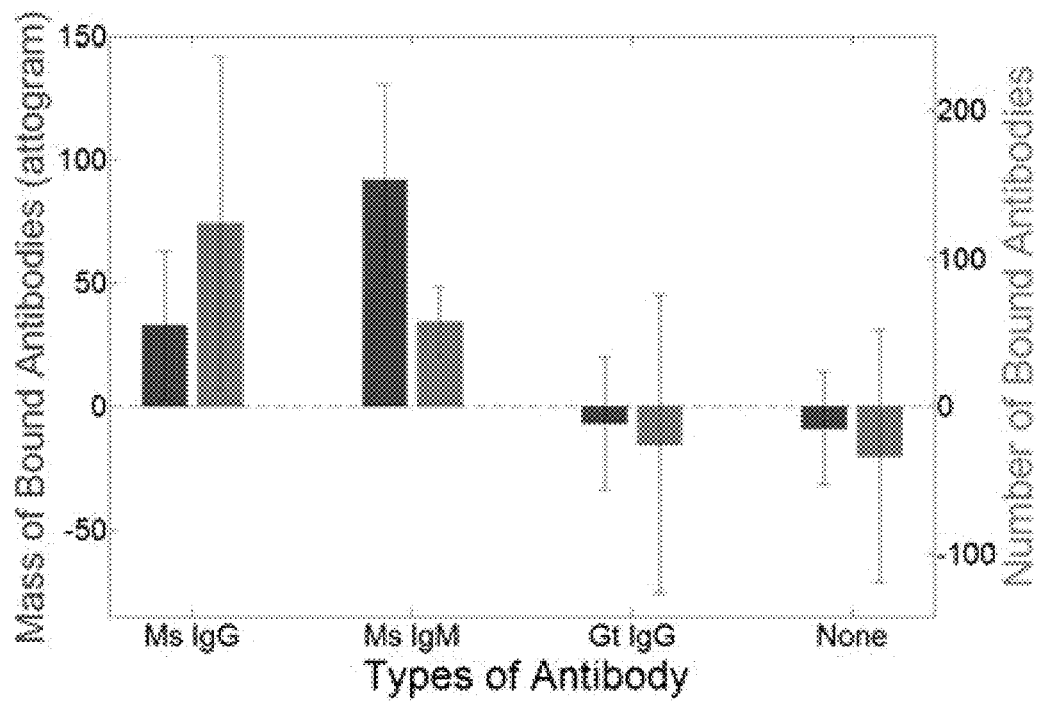
FIG. 7 is a graph of stoichiometries of antibodies to a colloid, in accordance with an embodiment.

Referring to FIG. 7, in one embodiment, are measurements of the stoichiometry of each binding event. The manufacturer-quoted binding capacity of coated IgG to polystyrene particles (Spherotech, Inc) is ≈117.4 IgGs (≈31.3 ag) per particle. The manufacturer-quoted binding capacity of mouse IgG (FITC-labeled) to coated anti-mouse IgG is ≈107.6 IgGs (≈28.7 ag) per particle. In comparison, the binding capacity measured in the affinity assay for mouse IgG was 124.0±112.7 IgGs (33.0±30.0 ag) per particle, whereas for mouse IgM it was 57.0±23.9 IgMs (91.8±38.5 ag) per particle. Despite the large uncertainties, the results of the binding capacity indicate a 1:1 binding ratio, consistent with the manufacturer-quoted binding capacity. Slightly larger binding capacity of the mouse IgG than the manufacturer-quoted one is likely because of unlabeled antibodies used in these experiments.

According to an embodiment, the methods and systems described herein are utilized to analyze the stoichiometry of the interaction between a first particle and two or more second particles. For example, the stoichiometry of an interacting antibody was examined. Specifically, the binding capacity of antibody coated on a polystyrene particle with 2.89 μg/mg of particles was used to determine stoichiometry of binding antibody from a radius change. The number of IgG per mg of particle was calculated as $N_{IgG} = M_{IgG,total}/M_{IgG} = 1.084 \times 10^{13}$ IgG/mg, where molecular weight of IgG is 160.5 kDa (=0.2665 ag). The number of polymer particles per mg are calculated as $N_{ps} = M_{ps,total}/M_{ps} = M_{ps,total}/(\rho_{ps}\pi D^2) = 9.241 \times 10^{10}$ particles/mg, where the density of polystyrene is 1.05 g/cm$^3$, and manufacturer-quoted diameter of particles is approximately 270 nm. Therefore the binding capacity of anti-mouse IgGs to a polymer particle is calculated to be 117.4 IgGs per particle. Volume occupied by the number of antibody (NIgG=117.4) to the volume of a IgG-coated layer (t=$\delta_{IgG}$=5.794 nm) determines the antibody density in a binding layer. Volume of an individual antibody is determined from dehydrated mass of an antibody as $V=d_{IgG\ (or\ IgM)}^3$, where $d_{IgG}$=5.79 nm and $d_{IgM}$=10.55 nm. The density was used to determine the volume of antibodies binding to a IgG-coated colloid with a radius increase resulting from the bindings. This allows for the determination of the total mass of bound antibodies, and thus the number of bound antibodies.

Example 2

Figure 8:
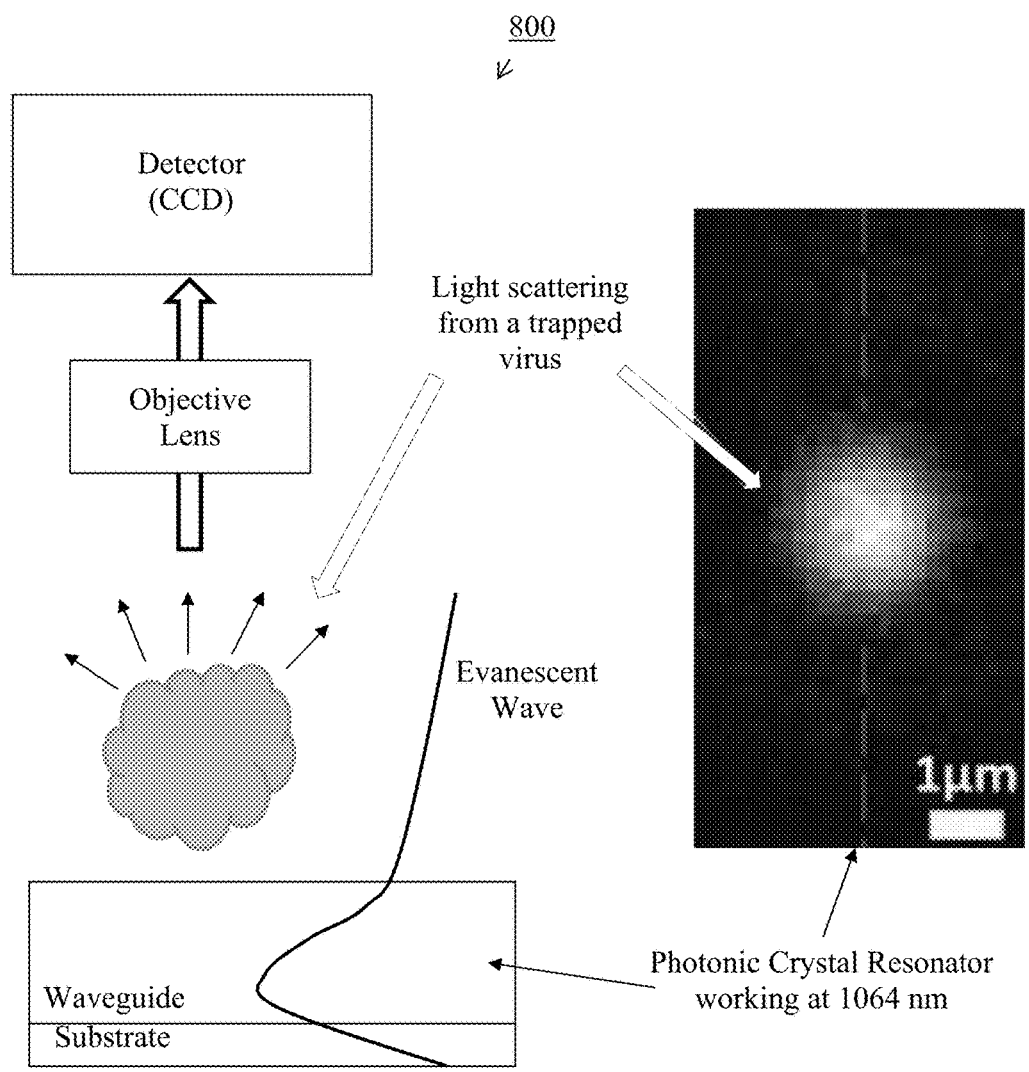
FIG. 8 is a schematic representation of an experimental setup of light scattering imaging for analyzing binding, where the inset shows a trapped virus particle, in accordance with an embodiment.

According to an embodiment, the near-field optical trap method and system can be utilized to investigate interactions between, for example, a pathogenic virus and its antibody. Understanding these interactions is vital to pathogen control and prevention. According to an embodiment, the specific antibody to a human influenza A virus was detected using the near-field light scattering technique. Referring to FIG. 8, in one embodiment, is a schematic representation of a system 800 for analyzing biomolecular interactions using a near-field light scattering method. The technique provides a detection method for pathogen identification without the need of labeling either of a virus or an antibody. Accordingly, the method can accurately measure affinity and stoichiometry of an anti-influenza antibody to the influenza virus. Further, sensitivity of the binding detection can be improved by trapping a smaller target particle like an influenza virus (D≈100 nm) than a 270-nm diameter IgG coated colloid.

Changes in power-normalized trap stiffness are compared for different solutions of mouse anti-influenza IgG, goat anti-rabbit IgG, and a buffer. The methods described above are utilized to correlate the power-normalized relative trap stiffness to the radius increase with a known initial diameter for $R_{inner}$ ($D_{virus} \approx 100$ nm). Affinity is indicated from a radius increase 7.6±1.1 nm in the solution of mouse anti-influenza IgG. The radius increase is attributed to the specific binding of anti-influenza IgG. Specificity is demonstrated by much smaller radius increases 0.2±1.7 nm and i 0.2±1.5 nm in the solution of an unspecific antibody (goat anti-rabbit IgG) and a buffer respectively. Compared to the previous assay, the sensitivity of binding detection to the unspecific binding was improved, which is attributed to the smaller size of viruses leading to a larger fractional polarizability change for a given bound layer, and to the better signal-to-noise ratio of the light scattering imaging technique.

The stoichiometry of the binding antibodies was also determined from the obtained measurements. The binding capacity of anti-influenza IgG to the virus is 6.8±1.1 ag (25.5±4.3 IgGs) per virus. In comparison, specificity is shown by much smaller binding of 0.2±1.4 ag (0.7±5.1 IgGs) and −0.1±1.1 ag (−0.5±4.3 IgGs) per virus in the solution of goat anti-rabbit IgG and a buffer respectively. While other techniques are capable of virus detection, the methods and systems described herein enable quantitative measurements of the binding capacity of an anti-influenza antibody to a single virus.

Sample Preparation

According to an embodiment, colloids and antibodies were diluted in a buffer solution of 1× phosphate buffered saline (PBS) containing 0.05% bovine serum albumin (BSA), and 0.05% Tween 20. For anti-influenza antibody 5 μl stock solution was diluted in 1 ml of the buffer solution, and concentration of all other antibodies in a diluted solution was 1 μg/ml, which is the typical limit of detection for numerous types of biosensors. Goat anti-mouse IgG coated fluorescent polystyrene particles (FITC, MFP-0252-5, $D_{mean} \approx 0.27$ μm) were purchased from Spherotech Inc. (Lake Forest, Ill.). Mouse IgG (MG300) and mouse IgM (MGM00) antibodies were from Invitrogen Corp. (Camarillo, Calif.). Goat anti-rabbit IgG (A10533) antibody was from Life Technologies (Carlsbad, Calif.). Swine-origin Human influenza A California/4/2009 (H1N1) virus (purified and UV-inactivated) was from Advanced Biotechnologies Inc. (Columbia, Md.). Mouse anti-influenza A H1N1 monoclonal IgG antibody (MAB8256) was purchased from EMD Millipore Corp (Temecular, Calif.). Other chemicals such as Superblock blocking buffer (37580), PBS (10× concentrate, P5493), bovine serum albumin (A9647), Tween 20 (P7949), were purchased from Sigma-Aldrich.

Imaging and Data Analysis

Image acquisition was performed by a Hamamatsu ORCA-ER CCD camera controlled by a Hamamatsu HCImage software. 40× objective (LUCPlanFL N, 0.60, ∞/0-2/FN22, UIS2) was used for both the fluorescence imaging and the near-field light scattering imaging. Fluorescent particles were imaged with excitation by a mercury arc lamp. Fluorescence imaging was optimized with an 842 nm blocking edge BrightLine short-pass filter for exposure time of 10 ms. Detection of near infrared at 1064 nm from the camera is accounted for manufacturer-quoted quantum efficiency of 0.45% (Hamamatsu Photonics). The light scattering imaging was optimized with a 641/75 nm BrightLine single-band bandpass filter (FF01-641/75-25, Transmission at 1064 nm, 2.6%) for exposure time of 20-100 μs, or a 628/40 nm BrightLine single-band bandpass filter (FF02-628/40-25, Transmission at 1064 nm, 0.2%) for exposure time of 0.7-2 ms.

Experimental Measurements

According to an embodiment, in measurements, experimental parameters such as power, number of instantaneous positions to determine the trap stiffness, and uncertainty of a measurement were characterized to obtain a reliable measurement of the trap stiffness. The critical power to optically trap a D 270 nm colloid ranged in 1.5-2 mW ($P_{TE}$) whereas that for D≈100 nm influenza A virus ranged in 3.5-5 mW ($P_{TE}$). Below this range the optical scattering force or hydrodynamic force exerted on a trapped particle destabilize the optical trap, either transporting the particle in the propagation direction of electromagnetic wave or losing the optical trap. In addition, power above the range caused sticking of a trapped particle on the resonator surface in which the trap stiffness ranged in $1.7<k_r<2.5$. In order to minimize external noise such as thermal excitation caused by long-time fluorescent excitation, observation time related to the number of instantaneous positions is optimized to be 12-25 sec for each measurement with exposure time 10 μs, resulting in $0.6<k_r<0.9$ otherwise. According to an embodiment, the detection method is based on fluctuation-based measurements that can involve external noises such as mechanical vibrations, detector noise, and thermal noise. Determination of the uncertainty caused by these factors describes signal-to-noise ratio, providing a more accurate assay analysis.

TEM Imaging

Transmission electron microscopy (TEM) image of a Human influenza A H1N1 virus was taken with the FEI Tecnai F20 in STEM mode in the Cornell Center for Materials Research Shared Facilities. A staining protocol was performed prior to TEM imaging. Observed size range of the viruses was consistent with the literature that the range is considered to be approximately 90-110 nm in diameter. Average size was estimated approximately 100 nm. The TEM image showed that the viruses retain viral morphology and hemagglutin (HA) in the viral envelope, allowing viable affinity assays with anti-influenza antibodies.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A label-free method for characterizing an interaction between a first unlabeled biomolecular particle and a second unlabeled biomolecular particle, the method comprising the steps of:

providing an optical trap system, the optical trap system comprising a photonic crystal resonator having a light source directed thereto for exciting the photonic crystal resonator and a camera positioned above a trapping site in the photonic crystal resonator;

radiating light from the light source in proximity of the trapping site in the photonic crystal resonator;

optically trapping the first unlabeled biomolecular particle with a first known refractive index in the photonic crystal resonator using light with a specific minimum power from the light source to induce trapping;

wherein the first unlabeled biomolecular particle has a known radius, $R_0$;

obtaining a first measurement of Brownian motion while the first unlabeled biomolecular particle is in the photonic crystal resonator based on light scattering captured by the camera from the first unlabeled biomolecular particle;

introducing the second unlabeled biomolecular particle with a second known refractive index into the photonic crystal resonator;

incubating the first and second unlabeled biomolecular particle under conditions suitable for binding said first and second unlabeled biomolecular particle to form a complex, wherein the second unlabeled biomolecular particle has a potential affinity for the first unlabeled biomolecular particle;

wherein the the first unlabeled particle has a second radius, $R'$ and $R'-R_0=\Delta R$;

optically trapping the first unlabeled biomolecular particle in the photonic crystal resonator using light with the specific minimum power from the light source to induce trapping after incubation;

wherein the first unlabeled biomolecular particle is a virus and the second unlabeled biomolecular particle is an antibody;

obtaining a second measurement of Brownian motion of the first unlabeled particle in the photonic crystal resonator after incubation based on light scattering captured by the camera from the first unlabeled biomolecular particle;

obtaining a relative Brownian motion measurement, defined as a comparison of the first and second measurements of Brownian motion, of the first unlabeled particle after incubation and based on light scattered by the first unlabeled particle captured by the camera;

analyzing a relationship between the relative Brownian motion measurement of the first unlabeled particle after incubation and $\Delta R$; and determining, using the relationship of the relative Brownian motion measurement of the first unlabeled particle with respect to $\Delta R$, a Brownian motion measurement of the photonic crystal resonator;

wherein said relationship provides indication whether a complex is formed.

\* \* \* \* \*